United States Patent
Olson et al.

(10) Patent No.: US 6,280,391 B1
(45) Date of Patent: Aug. 28, 2001

(54) METHOD AND APPARATUS FOR REMOVING BASELINE WANDER FROM AN EGG SIGNAL

(75) Inventors: Dana J. Olson, Kirkland; Dennis R. Seguine, Monroe, both of WA (US)

(73) Assignee: Physio-Control Manufacturing Corporation, Redmond, WA (US)

( * ) Notice: Subject to any disclaimer, the term of this patent is extended or adjusted under 35 U.S.C. 154(b) by 0 days.

(21) Appl. No.: 09/246,625

(22) Filed: Feb. 8, 1999

(51) Int. Cl.[7] .................................................. B61B 5/0428
(52) U.S. Cl. ................................................. 600/509; 607/5
(58) Field of Search .................................... 600/508, 509, 600/510, 515, 518, 521; 607/5

(56) References Cited

U.S. PATENT DOCUMENTS

| | | |
|---|---|---|
| 3,569,852 | 3/1971 | Berkovits . |
| 4,147,162 | 4/1979 | Gatzke . |
| 4,153,049 | 5/1979 | Gatzke et al. . |
| 4,194,511 | 3/1980 | Feldman . |
| 4,479,922 | 10/1984 | Haynes et al. . |
| 4,492,235 * | 1/1985 | Sitrick ................................. 128/705 |
| 4,494,551 | 1/1985 | Little, III et al. . |
| 5,042,026 | 8/1991 | Koike et al. . |
| 5,297,557 | 3/1994 | Reichl . |
| 5,318,036 | 6/1994 | Arand et al. . |
| 5,357,969 | 10/1994 | Herleikson . |
| 5,402,795 * | 4/1995 | Reichi ................................. 128/696 |
| 5,433,208 | 7/1995 | Lundstrom et al. . |
| 5,532,951 | 7/1996 | Ohlsson et al. . |
| 5,601,089 | 2/1997 | Bledsoe et al. . |
| 5,683,425 * | 11/1997 | Hauptmann .............................. 607/9 |
| 5,762,068 | 6/1998 | dePinto . |
| 5,772,603 | 6/1998 | Ohlsson et al. . |

FOREIGN PATENT DOCUMENTS

WO 93/05573  3/1993  (WO) .

OTHER PUBLICATIONS

Marques De Sa, J.P., "Digital FIR Filtering for Removal of ECG Baseline Wander," *Journal of Clinical Engineering*, Jul.–Sep. 1982, vol. 7, No. 3, pp. 235–240.

Angelidis, Em. and Diamessis, J.E., "A Parallel Interpolation Method for Designing FIR Digital Filters by Nonuniform Frequency Samples," Proceeding of IEEE International Conference on Acoustics, Speech, and Signal Processing, Apr. 27–30, 1993, III–105–III–108.

(List continued on next page.)

*Primary Examiner*—William E. Kamm
(74) *Attorney, Agent, or Firm*—Christensen O'Connor Johnson Kindness PLLC (57) ABSTRACT

A baseline wander filter (BWF) with linear phase response for an ECG signal measuring system includes two cascaded box car FIR filters to estimate the baseline wander. The cascaded box car filters form, in effect, a triangular FIR filter that generates a weighted sliding window average of the input samples to serve as the estimated baseline wander. The estimated baseline wander samples generated by the BWF are then subtracted from the corresponding input ECG samples. The boxcar filters can be designed to avoid multiplication by adding the samples and dividing the resulting sum by the number of coefficients. By choosing the number of coefficients as a power of two, binary division can be performed by shifting the bits of the resulting sum to the right. Accordingly, the present invention avoids the relatively large computational load of conventional FIR filter-based systems. The BWF can be implemented in software in which each boxcar filter uses an accumulator data structure that generates the sum of the previous N samples. When adding the next sample to the sum, it subtracts the Nth previous sample. The output sample of the BWF is equal to the value in the sum buffer, appropriately shifted.

20 Claims, 6 Drawing Sheets

OTHER PUBLICATIONS

Coradine, L.C., Romano, J.M.T. and Bellanger, MG., "Adaptive Filtering in Cascade Form Using a Fast Multichannel RLS Algorithm," *IEEE Transactions on Circuits and Systems II: Analog and Digital Signal Processing*, vol. 44, No. 9, Sep. 1997, pp. 757–762.

Vanderkooy, John and Lipshitz, Stanley P., *J. Audio Eng. Soc.*, "Resolution Below the Least Significant Bit in Digital Systems with Dither," vol. 32, No. 3, Mar. 1984.

* cited by examiner

METHOD AND APPARATUS FOR REMOVING BASELINE WANDER FROM AN EGG SIGNAL

FIELD OF THE INVENTION

The present invention relates to ECG measuring systems and, more particularly, to ECG measuring systems using analog-to-digital processing.

BACKGROUND INFORMATION

Figure 1:
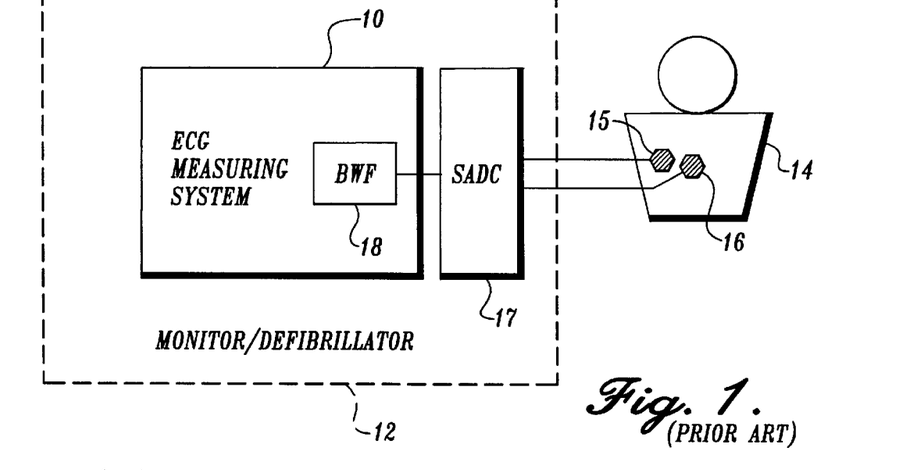
FIG. 1 is a diagram illustrative of a typical ECG signal measuring system.

When providing emergency cardiac patient care, it is essential to generate the patient's electro-cardio graph (ECG) quickly and accurately for proper diagnosis and successful treatment. A typical ECG signal measuring system 10 is shown in FIG. 1. In this example, ECG signal measuring system 10 is part of diagnostic-quality monitor/defibrillator 12. To measure the ECG signal of a patient 14, ECG signal measuring system 10 is coupled to patient 14 through electrodes 15 and 16 and a signal acquisition and digitizing circuit 17. Signal acquisition and digitizing circuit 17 is a standard circuit configured to receive the analog ECG signals from the electrodes and convert this signal into a digital signal. ECG signal measuring system also includes a baseline wander filter (BWF) 18.

Large amplitude, low-frequency, non-physiological signals, commonly referred to as baseline wander, are generally sensed along with the patient's ECG. There are several sources of baseline wander including; DC bias currents, patient movement and changing patient impedance. Several of the sources of baseline wander are described further below.

Figure 2:
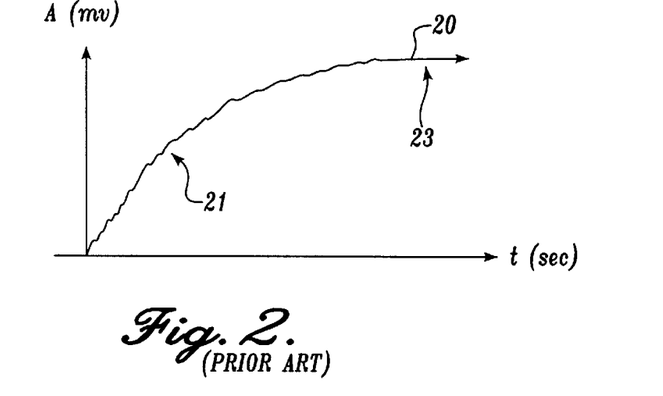
FIG. 2 is a graph illustrative of an ECG generated by a conventional ECG signal measuring system in applying electrodes to a patient.

ECG signal measuring systems used for emergency medical applications typically use a DC bias current to detect disconnected electrode leads. This current interacts with the patient's impedance to cause a relatively high amplitude but low frequency signal that is superimposed on the relatively low voltage ECG signal when electrodes 15 and 16 are initially applied to patient 14. For convenience, this signal is referred to herein as the bias current signal. This bias current signal is illustrated in FIG. 2 by a curve 20. As can be seen in FIG. 2, an initial portion 21 of curve 20 has a relatively large rate of change. The bias current signal eventually begins to stabilize, as indicated by a portion 23 of curve 20. The bias current signal results in a significant rate of change of the combined input signal (i.e., the baseline wander combined with the patient ECG signal) during the initial period. This rate of change of the combined input signal is referred to herein as the slew rate. When the bias current signal eventually starts to stabilize, the slew rate of the combined input signal is reduced.

Baseline wander can also be caused by movement of patient 14 or electrodes 15 or 16 that disturbs the electrical connection of electrodes 15 and 16 to patient 14. This movement can result in a significant change in the impedance presented to ECG signal measuring system 10. This change in impedance can result in a change in the bias current signal, which results in a change in the level of the combined input signal.

Baseline wander can also be caused by interaction of the bias current with changing patient impedance caused by the electrodes forming a better electrical connection to the patient over time.

Figure 3:
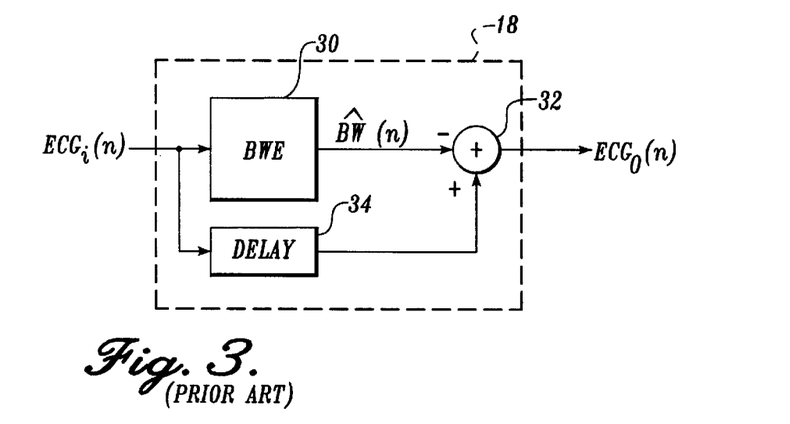
FIG. 3 is a block diagram illustrative of a conventional IIR filter-based BWF.

Generally, the baseline wander is estimated and the estimate is subtracted from the combined signal before displaying the output ECG. One conventional system for estimating baseline wander is illustrated in FIG. 3. FIG. 3 is a functional block diagram illustrative of conventional BWF 18 (FIG. 1) for use in a digital ECG measuring system. BWF 18 includes an infinite impulse response (IIR) baseline wander estimator (BWE) 30, an adder 32 and a delay circuit 34. BWE 30 is connected to receive input ECG samples, denoted $ECG_i(n)$, and output an average of the samples that represents the estimated baseline wander samples, denoted $BW(n)$. Delay circuit 34 also receives $ECG_i(n)$, and delays each sample by the delay of BWE 30. In this way, each $BW(n)$ sample is synchronized with the corresponding $ECG_i(n)$ sample. Adder 32 receives each estimated baseline wander $BW(n)$ sample and subtracts it from the corresponding input ECG sample $ECG_i(n)$, thereby generating output ECG samples, $ECG_o(n)$.

One problem with using a BWE based on an IIR filter is that, in some conventional systems, the IIR filter normally provides non-linear phase response. To linearize the phase response in these conventional systems, the data must be filtered, then the output samples must be reversed in order, and filtered through the IIR filter again. This "forward-backward" operation adds delay to the process, and requires that the data be processed in batches. Thus, each filtered "batch" must then be appended to the previous filtered "batch", which, undesirably, tends to cause discontinuities in the output ECG. Other conventional systems that use IIR filters to remove baseline wander employ a slew-rate limiter to clip portions of the input ECG signal. The slew-rate limiter adds complexity and cost to the system. Generally, these conventional systems use IIR filters to avoid the relatively high computation load of conventional finite impulse response (FIR) systems. Thus, there is a need for a BWE that is computationally efficient, has linear phase response, and does not require an additional circuitry such as a slew-rate limiter.

SUMMARY

In accordance with the present invention, an efficient, low-cost BWE with linear phase response for an ECG signal measuring system is provided. In one aspect of the present invention, the BWE includes two cascaded box car FIR filters to estimate the baseline wander. The cascaded box car filters form, in effect, a triangular FIR filter (i.e., the co-efficients form a triangular profile), which generates a weighted sliding window average of the input samples to serve as the estimated baseline wander. The estimated baseline wander samples generated by the BWE are then subtracted from the corresponding input ECG samples. This aspect of the present invention significantly reduces the computational burden of the FIR filter implementation because the boxcar filters can be designed to avoid multiplication. In one embodiment, the samples are added and the resulting sum is divided by the number of coefficients (e.g., N). By choosing the number of coefficients as a power of two (i.e., $N=2^n$), binary division can be performed by shifting the bits of the resulting sum by n places to the right. Accordingly, the present invention avoids the relatively large computational load of conventional FIR filter-based systems. In addition, this aspect of the present invention allows the BWE to operate on the input samples continuously as they are received, thereby avoiding the discontinuities caused by batch processing required by some conventional IIR filter-based systems. In addition, the input ECG need not be clipped as in other conventional IIR filter-based systems.

In another aspect of the present invention, the BWE is implemented in software. Each boxcar filter uses an accumulator data structure that generates the sum of the previous N samples. When adding the next sample to the sum, it subtracts the Nth previous sample. For example, each sample may be stored in a circular buffer and added to a value in a sum buffer. Before storing the current sample into the circular buffer, the existing sample is subtracted from the value in the sum buffer. The output sample would then be equal to the value in the sum buffer, appropriately shifted. Alternatively, the shifting may be performed after being processed by the second box filter.

DETAILED DESCRIPTION

Figure 4:
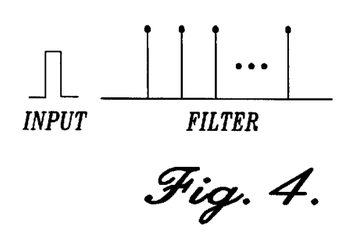
FIG. 4 is a diagram illustrative of the coefficients of a boxcar FIR filter.
Figure 5:
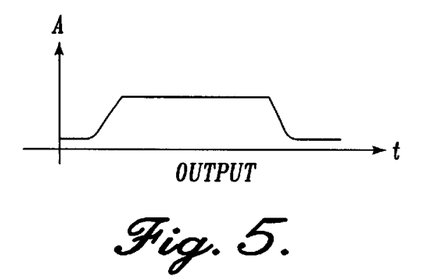
FIG. 5 is a graph illustrative of the pulse response of the boxcar filter depicted in FIG. 4.

FIG. 4 is a diagram illustrative of the coefficients of a boxcar FIR filter. As is well known, a boxcar filter has a finite number of equal coefficients. In response to a sampled rectangular pulse (i.e., a finite sequence of samples having the same value), a boxcar filter outputs a sequence having an envelope as illustrated in FIG. 5. More specifically, the output samples increase linearly before leveling at constant value. The number of samples in linearly increasing portion of the output sequence is equal to the number of coefficients of the boxcar filter. After the last sample of the sequence enters the boxcar filter, the output samples begin linearly decreasing, in a symmetrically opposite manner to the increasing magnitude at the front end of the response. As will be appreciated by those skilled in the art, the "slopes" and sharp edges at either end of the output sequence are undesirable because they may contain features that are detected as ECG signals. What is desired in the FIR filter for use in the BWE is a response that smoothly masks the input pulse.

Figure 6:
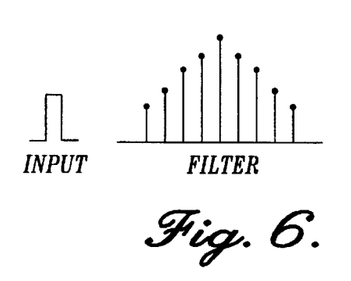
FIG. 6 is a graph illustrative of the coefficients of a triangular filter.
Figure 7:
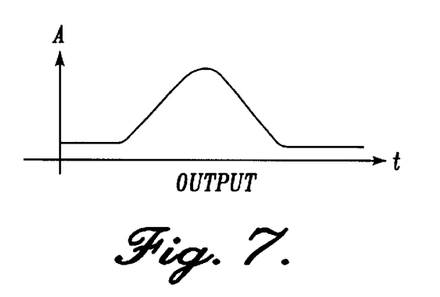
FIG. 7 is a graph illustrative of the pulse response of the triangular filter depicted in FIG. 6.

One such FIR filter is a filter having coefficients as illustrated in FIG. 6, which has an envelope resembling a triangle (referred to herein as a triangular filter). In response to a sampled pulse, the triangular filter generates a response as illustrated in FIG. 7. Accordingly, the response of the triangular filter accurately estimates the baseline wander and does not output sharp slopes and edges in response to pulses.

Figure 8:
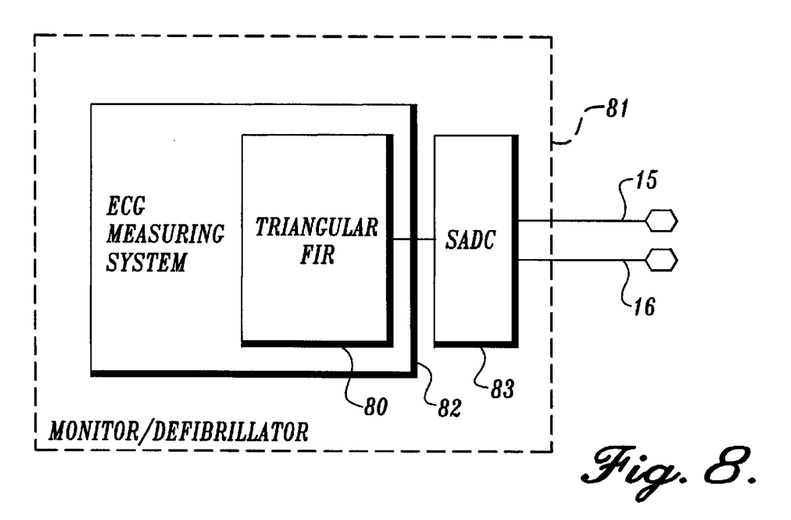
FIG. 8 is a block diagram illustrative of a FIR filter-based BWF, according to one embodiment of the present invention.

FIG. 8 is a block diagram illustrative of a BWF 80, according to one embodiment of the present invention. For clarity, the same reference numbers are used in the drawings to indicate elements having the same or similar function or structure. In this embodiment, BWF 80 is part of a monitor/defibrillator 81 that includes ECG measuring system 82. ECG measuring system 82 measures the ECG of patient 14 (FIG. 1) through the use of electrodes 15 and 16 which are applied to patient 14 as described above for ECG measuring system 10 (FIG. 1). The measured ECG signal is received and digitized by a signal acquisition and digitizing circuit 83. In this embodiment, the measured ECG signal is sampled at 5000 samples-per-second using a twelve-bit analog-to-digital converter. Signal acquisition and digitizing circuit 83 may also be configured to perform some initial signal processing, such as anti-aliasing filtering, high-pass filtering and decimation of the samples. However, ECG measuring system 82 differs from ECG measuring system 10 (FIG. 1) in that BWF 80 is implemented with an triangular FIR filter as described above in conjunction with FIG. 6, instead of an IIR filter as in BWF 18 (FIG. 1).

Long term averaging of the input samples can be used to estimate baseline wander because the ECG signal portion of the input samples tends to be of short duration and cancelled out in a long average. However, the baseline wander may be of large amplitude but with a relatively slow rate of change. Thus, an average of a group of input samples taken over a period of time (e.g., 4 seconds) relatively accurately estimates the baseline wander at the center of that time period.

Figure 9:
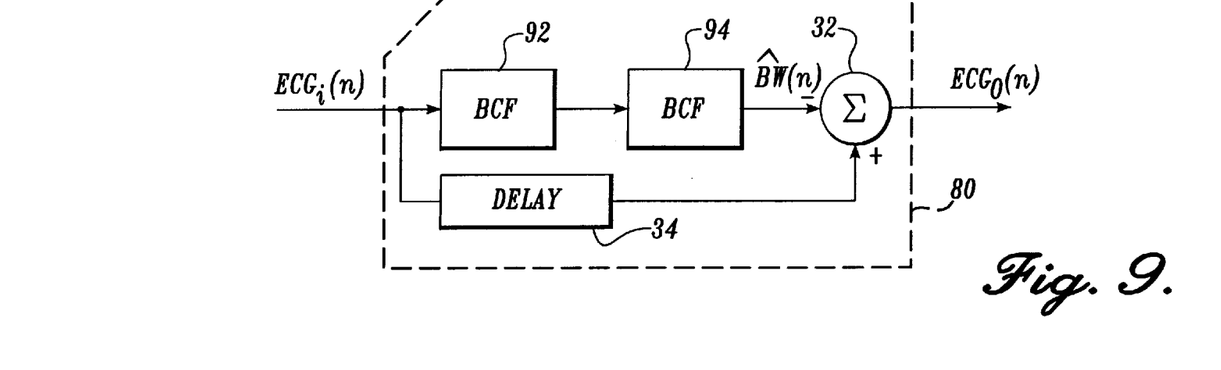
FIG. 9 is a functional block diagram illustrative of a cascaded boxcar filter implementation of the BWF of FIG. 8, according to another embodiment of the present invention.

FIG. 9 is a functional block diagram illustrative of BWF 80 implemented with cascaded boxcar filters, according to one embodiment of the present invention. In this embodiment, BWF 80 includes a boxcar filter (BCF) 92, a BCF 94, adder 32 and delay circuit 34. BWF 80 is connected to receive input ECG samples $ECG_i(n)$ and generate output ECG samples $ECG_o(n)$. Generally, input ECG samples $ECG_i(n)$ have been sampled from an ECG signal that is sensed from patient 14, filtered through an anti-aliasing filter (not shown) and high pass filtered to attenuate a significant portion of the baseline wander. An example of this front-end processing is disclosed in copending and commonly-assigned U.S. patent application Ser. No. 09/232,044, entitled "Method And Apparatus For Increasing The Low Frequency Dynamic Range Of A Digital ECG Measuring System" by D. Olson et al., filed Jan. 15, 1999. The system described in the aforementioned Ser. No. 09/232,044 application can be advantageously used in conjunction with the present invention, although the present invention can be used with other conventional systems as well.

This embodiment of BWF 80 is interconnected as follows. BCF 92 and delay circuit 34 are connected to receive the input ECG samples $ECG_i(n)$. The output port of BCF 92 is connected to the input port of BCF 94. The output ports of BCF 94 and delay circuit 34 are connected to a negative input port and positive input port of adder 32, respectively.

BWF 80 operates as follows. In this embodiment, BCFs 92 and 94 are both 1025-tap FIR filters with all of the coefficients being equal to one. Due to the cascade configuration, the delay through BCFs 92 and 94 is 2050 cycles. Delay circuit 34 is configured to provide a delay of 1025 cycles. Each boxcar filter delays the signal by half of its width, thus the two cascaded filters have a delay of 1025 samples. Thus, there is a delay of only 1025 cycles before BWF 80 begins generating output ECG samples $ECG_o(n)$. As described above in conjunction with FIGS. 6 and 7, the triangular filter implementation of BWF 80 generates a relatively accurate estimate of the baseline wander.

Those skilled in the art of digital filters will appreciate that the cascaded BCFs 92 and 94 form, in effect, a triangular FIR filter. This "triangular filter" generates a weighted sliding window average of the input samples to serve as the estimated baseline wander. Adder 32 then subtracts the estimated baseline wander samples generated by this "triangular filter" from the input ECG samples delayed by delay circuit 34. In this embodiment, the triangular filter is implemented in software. Because cascaded BCFs are used to implement the triangular filter as described below, the computational burden of calculating the filter output samples is significantly reduced compared to standard FIR implementations.

To calculate a BCF output sample of an N tap BCF, the N latest input samples are added and the resulting sum is divided by N. More specifically, the BCFs can be designed to avoid multiplication as follows. By setting the coefficient gain to one, no multiplication is required at the taps. Further, by setting the number of coefficients close to a power of two (i.e., $N=2^n$), binary division can be performed by shifting the bits of the resulting sum by n places to the right. Accordingly, the present invention avoids the relatively large computational load of conventional FIR filter-based systems. In this embodiment, the BCFs each have 1025 coefficients (i.e., $2^{10}$) with the coefficients all being equal to one. Consequently, each BCF output sample requires three additions and one right shift by 10 bits.

A further advantage of the present invention is that FIR implementation of BWF 80 allows BWF 80 to operate on the input samples continuously as they are received, thereby avoiding the discontinuities caused by batch processing required by some conventional IIR filter-based systems. In addition, the input ECG need not be clipped as in other conventional IIR filter-based systems.

Figure 10:
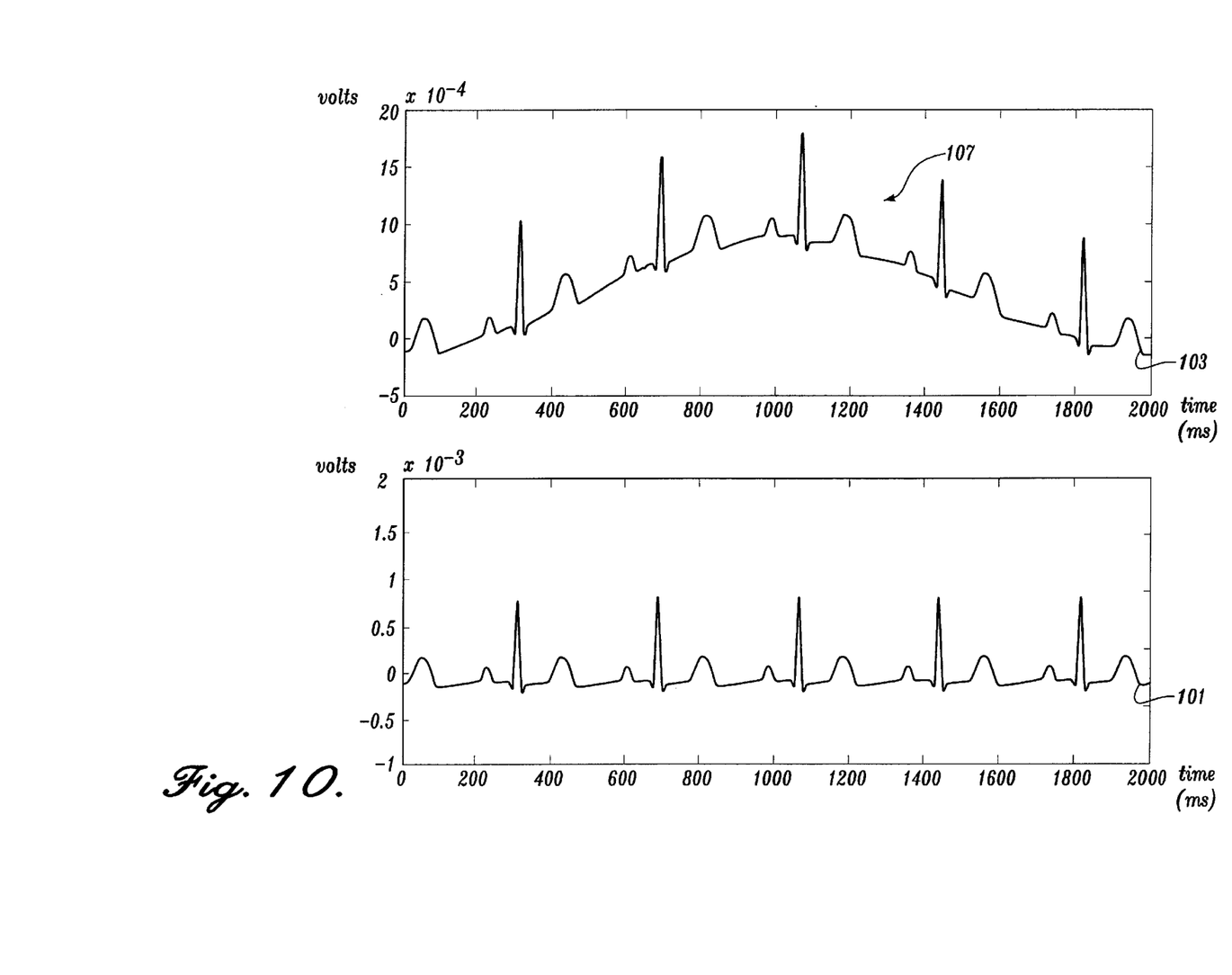
FIG. 10 is a graph illustrative of an ECG waveform with baseline wander compared to the ECG waveform recovered with a BWF.

FIG. 10 is a graph illustrative of an ECG waveform 101 generated using BWF 80 (FIG. 8) from an input ECG signal with baseline wander 103. Waveform 103 is an exemplary input waveform having a relatively large perturbation 107 caused by connecting electrodes 15 and 16 (FIG. 1). In this example, perturbation 107 is manifested as a relatively large "hump" in the input ECG signal. Waveform 101 was generated in response to waveform 103 using a commercially available simulation tool configured to simulate BWF 80. As can be seen, waveform 101 is a substantially normal ECG waveform despite perturbation 107 in the input ECG signal represented by waveform 103.

Figure 11:
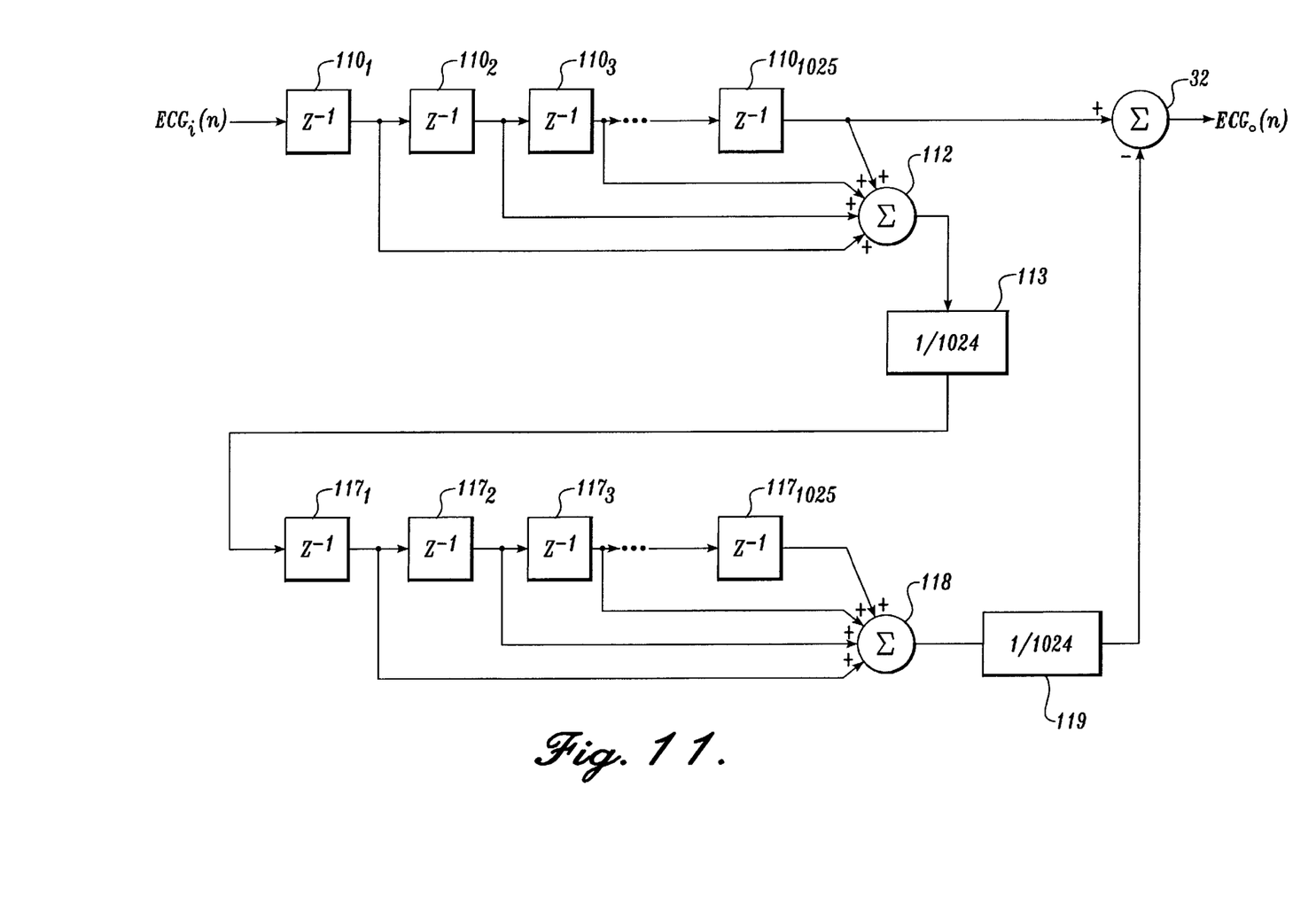
FIG. 11 is a more detailed block diagram illustrative of the BWF of FIG. 8, according to another embodiment of the present invention.

FIG. 11 is a more detailed block diagram illustrative of BWF 80 (FIG. 8), according to another embodiment of the present invention. In this embodiment, BCF 92 includes cascaded delay stages $110_1$–$110_{1025}$, an adder 112 connected to receive the output samples of delay stages $110_1$–$110_{1025}$, and a divider 113 connected to the output port of adder 112. Divider 113 is configured to divide the output sample of adder 112 by 1024. In this embodiment, 1025 points are used in the delay line rather than 1024 to allow storage processing blocks of five points. This gives a filter gain of 1025/1024.

Those skilled in the art of digital filters will appreciate that cascaded delay stages $110_1$–$110_{1025}$ together with adder 112 and divider 113 form a common implementation of a FIR boxcar filter that generates the unweighted mean of 1025 samples. The output port of delay stage $110_{1025}$ is connected to a positive input port of adder 32. BCF 94 includes cascaded delay stages $117_1$–$117_{1025}$, an adder 118 connected to receive the output samples of delay stages $117_1$–$117_{1025}$, and a divider 119. Divider 119 is configured to divide the output sample of adder 118 by 1024. The output port of divider 119 is connected to a negative input port of adder 32. This embodiment of BWF 80 operates as described above in conjunction with FIG. 9. Of course, in other embodiments, different numbers of delay stages can be used as desired to achieve an optimal accuracy and throughput for the particular application.

Figure 12:
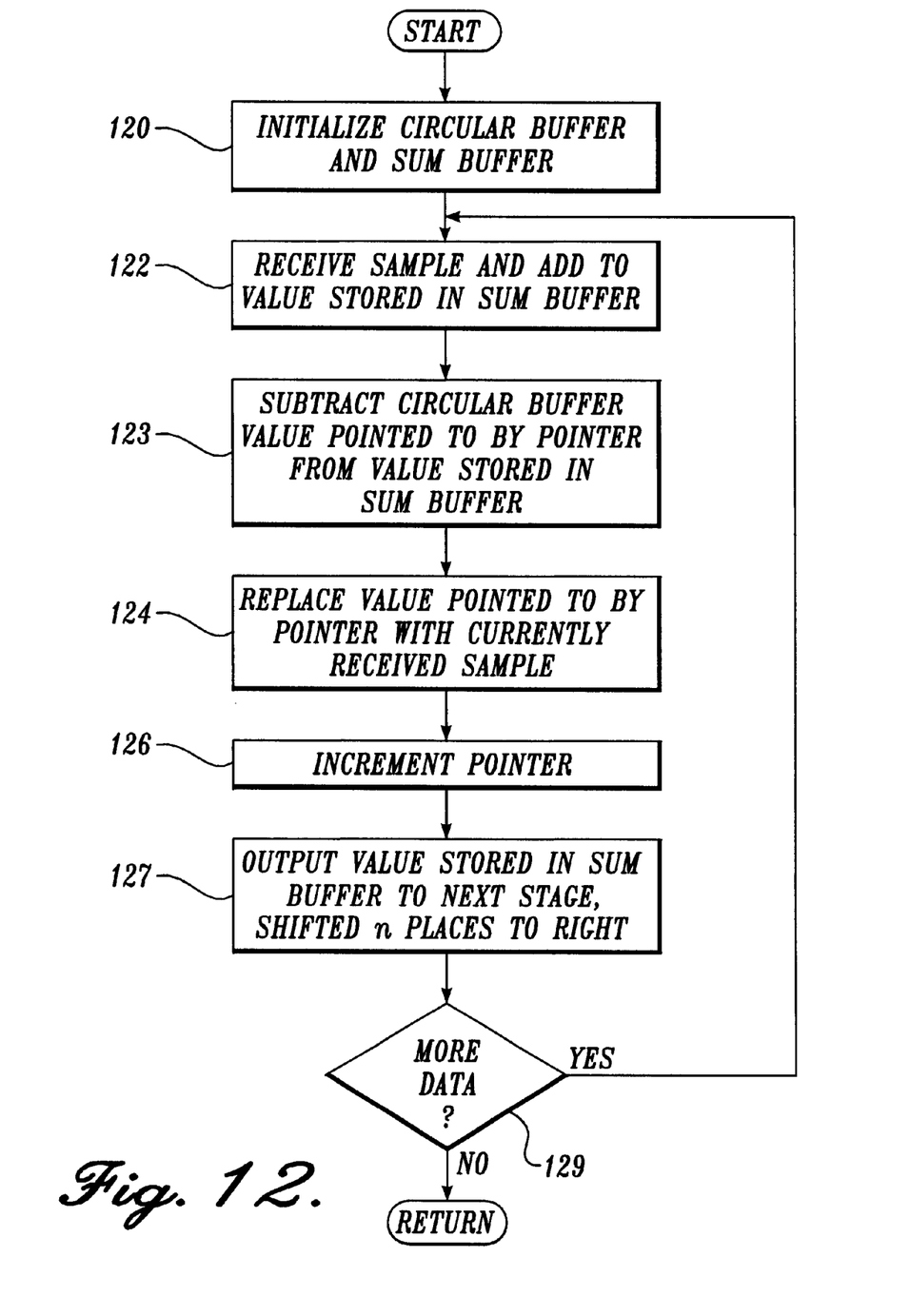
FIG. 12 is a flow diagram illustrative of a software implementation of a boxcar filter, according to one embodiment of the present invention.
Figure 13:
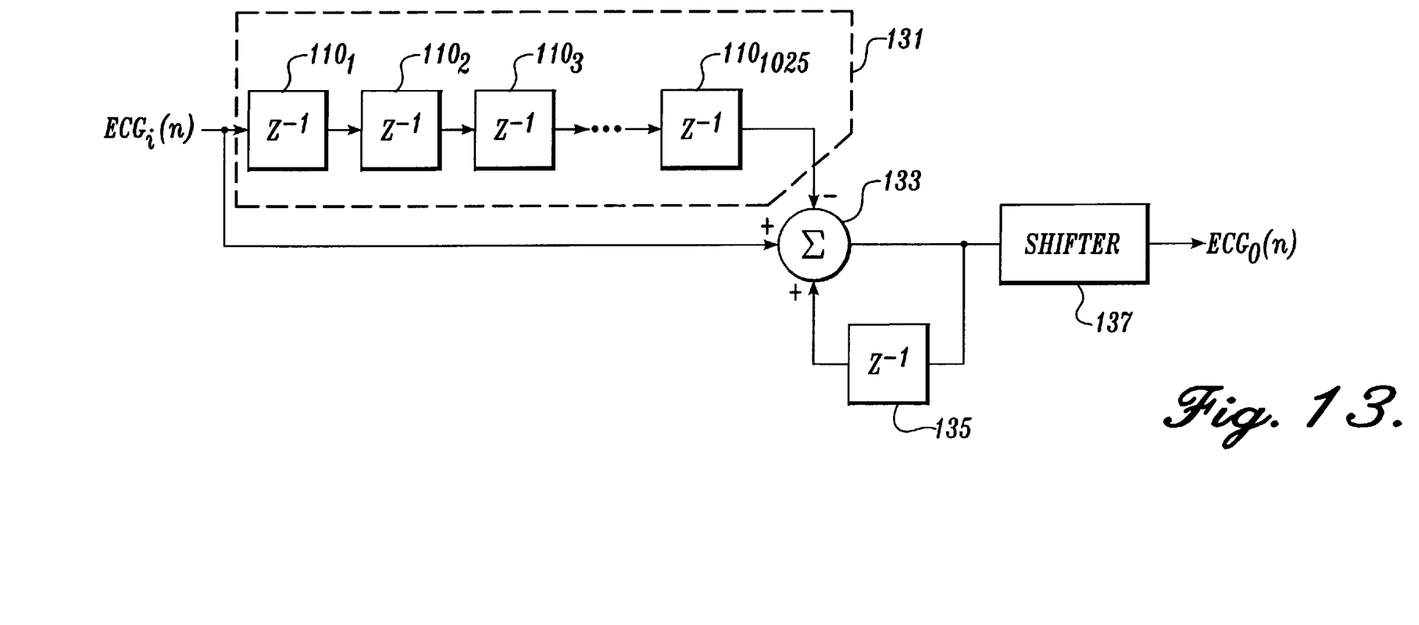
FIG. 13 is a detailed block diagram of a single computationally efficient box car FIR filter, according to another embodiment of the present invention.

FIG. 13 is a block diagram of an alternative embodiment of BWF 80 (FIG. 8). This embodiment includes a 1025-stage delay line 131, a summer 133, a delay stage 135, and a shifter 137. Delay line 131 is connected to receive the input samples and output the delayed samples to summer 133. Summer 131 is also connected to receive the current input sample and its own previous output sample (from delay stage 135, which is connected to receive the output sum of summer 133). Summer 133 is configured to add the current input sample to the summer's previous output sum, and subtract the $1025^{th}$ previous input sample. Shifter 137 is connected to receive the output sum from summer 133 and shift the sum by ten places to the right. This function can be implemented in software as described below in conjunction with FIG. 12.

FIG. 12 is a flow diagram illustrative of a software implementation of BCF 92 (FIG. 9), according to one embodiment of the present invention. In one embodiment, this software implementation in used in a LIFEPAK 12 monitor/defibrillator, available from Physio-Control Manufacturing Corporation, Redmond, Wash. This embodiment of BCF 92 includes a circular buffer data structure and a sum buffer. The sum buffer is a variable that is selected to store the sum of the latest 1025 sample values received by BCF 92. The circular buffer data structure uses a pointer to point to one of the N memory locations of the circular buffer. In this embodiment, N is equal to 1025. In a circular buffer, after the location is accessed, the pointer is typically incremented to point to the next memory location. After the last memory location of the circular buffer is accessed, the pointer typically returns to point once more at the first memory location.

When BCF 92 first starts operating, a step 120 is performed to initialize the circular buffer and the sum buffer. After initialization, the circular buffer and the sum buffer contain only zeros and the pointer points to the first memory location of the circular buffer.

In a next step 122, BCF 92 receives an input sample. The value of the sample is added to the current value stored in the sum buffer and the new sum is stored in the sum buffer. In a step 123, the value currently pointed to in the circular buffer is subtracted from the value in the sum buffer. This operation, in effect, subtracts the oldest sample from the sum, thereby helping to implement the sliding window running average function of BCF 92. In a step 124, the value stored in the location pointed to by the pointer is then updated with the received sample. Alternatively, step 123 may be performed before step 122, as long as the current memory location of the circular buffer is not updated before the current value of that memory location is subtracted from the sum buffer.

Then in a step 126, the pointer is incremented to point to the next memory location of the circular buffer. In a step 127, the updated sum in the sum buffer, shifted by n places to the right, is sent to the BCC's output port. In particular, the updated sum is shifted by an amount to achieve the desired division. In this embodiment, n is equal to ten because the sum should be divided by 1024 to compensate for gain realized by summing 1025 samples. Step 126 may be performed after step 127 in an alternative embodiment. Then in a step 129, the process returns to step 122 if there is another input sample to process or else returns to other tasks. BCF 94 (FIG. 9), being substantially identical to BCF 92, operates in essentially the same manner as described above for BCF 92.

To summarize, each BCF uses, in effect, an accumulator-type data structure that generates the sum of the previous N samples. When adding the next sample to the sum, the BCF subtracts the oldest of the previous N samples. The output sample of the BCF is equal to the value in the sum buffer, appropriately shifted. Alternatively, the first BCF may perform no shifting while the second BCF shifts its output sample by 2n.

The embodiments of the baseline wander filter system described above are illustrative of the principles of the present invention and are not intended to limit the invention to the particular embodiments described. For example, in light of the present disclosure, those skilled in the art can devise, without undue experimentation, embodiments using different implementations of the boxcar filters, including different numbers of taps. In addition, those skilled in the art, in light of the present disclosure, can adjust the sampling rate and decimation ratio to accommodate different output ECG signal frequency bandwidths and low-end bands. For example, subsequent application of additional BCFs would further smooth the line of effective FIR coefficients, thereby smoothing the pulse response. The number of BCFs and their numbers of taps can be adjusted to create alternative filter functions. Further, other embodiments may be adapted for use with other multiple lead ECG monitoring systems (e.g., twelve-lead systems). Accordingly, while the preferred embodiment of the invention has been illustrated and described, it will be appreciated that various changes can be made therein without departing from the spirit and scope of the invention.

We claim:

1. A method of removing baseline wander from a sensed ECG signal, the method comprising:

receiving a plurality of input ECG samples taken from the sensed ECG signal;

filtering the plurality of input ECG samples with a triangular finite impulse response (FIR) filter, wherein the filtered input ECG samples serve as a plurality of estimated baseline wander samples;

delaying the plurality of input ECG samples with a delay circuit, wherein the delayed input ECG samples serve as a plurality of delayed input ECG samples; and subtracting an estimated baseline wander sample of the plurality of the estimated baseline wander samples from a delayed input ECG sample from the plurality of delayed input ECG samples, the difference serving as an output ECG sample.

2. The method of claim 1 wherein filtering the plurality of input ECG samples with a triangular FIR filter comprises:

filtering the plurality of input ECG samples with a first boxcar filter (BCF), wherein the filtered plurality of input ECG samples serves as a plurality of intermediate samples; and filtering the plurality of intermediate samples with a second BCF, the filtered plurality of intermediate samples serves as the plurality of estimated baseline wander samples.

3. The method of claim 2 wherein filtering the plurality of input ECG samples with the first BCF comprises:

adding an Ath input ECG sample of the plurality of input ECG samples to a first sum and subtracting a (A−N)th input ECG sample of the plurality of input ECG samples from the first sum, wherein the first sum represents the sum of the Ath, (A−1)th, . . . (A−N+1)th input ECG samples of the plurality of input ECG samples, A and N being positive integers, A being greater than N; and dividing the first sum by N to provide an intermediate sample of the plurality of intermediate samples.

4. The method of claim 3 wherein filtering the plurality of intermediate samples with the second BCF comprises:

adding a $\tilde{A}$th intermediate sample of the plurality of intermediate samples to a second sum and subtracting a $(\tilde{A}-N)$th intermediate sample of the plurality of intermediate samples from the second sum, wherein the second sum represents the sum of the $\tilde{A}$th, $(\tilde{A}-1)$th, . . . $(\tilde{A}-N+1)$th intermediate samples of the plurality of intermediate samples, $\tilde{A}$ being a positive integer greater than N; and dividing the second sum by N to provide an estimated baseline wander sample of the plurality of estimated baseline wander samples.

5. The method of claim 4 wherein the delay circuit provides a delay of N+1 cycles.

6. The method of claim 5 wherein N is equal to 1024.

7. A filter for removing baseline wander from a sensed ECG signal, the filter comprising:

a triangular finite impulse response (FIR) filter, wherein the triangular FIR filter is configured to filter the plurality of input ECG samples, the filtered input ECG samples serving as a plurality of estimated baseline wander samples;

a delay circuit coupled to receive the plurality of input ECG samples, wherein the delay circuit is configured to delay the plurality of ECG input samples, the delayed input ECG samples serving as a plurality of delayed input ECG samples; and a logic circuit coupled to the triangular FIR filter and the delay circuit, wherein the logic circuit is configured to subtract an estimated baseline wander sample of the plurality of the estimated baseline wander samples from a delayed input ECG sample from the plurality of delayed input ECG samples, the difference serving as an output ECG sample.

8. The filter of claim 7 wherein the triangular FIR filter comprises:

a first boxcar filter (BCF) configured to filter the plurality of input ECG samples, wherein the filtered plurality of input ECG samples serves as a plurality of intermediate samples; and a second BCF configured to filter the plurality of intermediate samples, the filtered plurality of intermediate samples serves as the plurality of estimated baseline wander samples.

9. The filter of claim 8 the first BCF is further configured to:

add an input ECG sample of the plurality of input ECG samples to a first sum and subtract a (A−N)th input ECG sample of the plurality of input ECG samples from the first sum, wherein the first sum represents the sum of the Ath, (A−1)th, . . . (A−N+1)th input ECG samples of the plurality of input ECG samples, A and N being positive integers, A being greater than N; and divide the first sum by N to provide an intermediate sample of the plurality of intermediate samples.

10. The filter of claim 9 wherein the second BCF is further configured to:

add an $\tilde{A}$th intermediate sample of the plurality of intermediate samples to a second sum and subtracting an ($\tilde{A}$−N)th intermediate sample of the plurality of intermediate samples from the second sum, wherein the second sum represents the sum of the $\tilde{A}$th, ($\tilde{A}$−1)th, . . . ($\tilde{A}$−N+1)th intermediate samples of the plurality of intermediate samples, $\tilde{A}$ being a positive integer greater than N; and divide the second sum by N to provide an estimated baseline wander sample of the plurality of estimated baseline wander samples.

11. The filter of claim 10 wherein the delay circuit provides a delay of N+1 cycles.

12. The filter of claim 11 wherein N is equal to 1024.

13. The filter of claim 7 wherein the filter is implemented in software.

14. A defibrillator configured to measure a patient's ECG signal in conjunction with providing a defibrillation pulse, the defibrillator comprising:

a pair of electrodes configured to be coupled to the patient;

a signal acquisition and digitizing circuit coupled to the pair of electrodes; and an ECG measuring system coupled to the signal acquisition and digitizing circuit, the ECG measuring system including:

a triangular finite impulse response (FIR) filter, wherein the triangular FIR filter is configured to filter the plurality of input ECG samples, the filtered input ECG samples serving as a plurality of estimated baseline wander samples, a delay circuit coupled to receive the plurality of input ECG samples, wherein the delay circuit is configured to delay the plurality of ECG input samples, the delayed input ECG samples serving as a plurality of delayed input ECG samples, and a logic circuit coupled to the triangular FIR filter and the delay circuit, wherein the logic circuit is configured to subtract an estimated baseline wander sample of the plurality of the estimated baseline wander samples from a delayed input ECG sample from the plurality of delayed input ECG samples, the difference serving as an output ECG sample.

15. The defibrillator of claim 14 wherein the triangular FIR filter comprises:

a first boxcar filter (BCF) configured to filter the plurality of input ECG samples, wherein the filtered plurality of input ECG samples serves as a plurality of intermediate samples; and a second BCF configured to filter the plurality of intermediate samples, the filtered plurality of intermediate samples serves as the plurality of estimated baseline wander samples.

16. The defibrillator of claim 15 the first BCF is further configured to:

add an input ECG sample of the plurality of input ECG samples to a first sum and subtract a (A−N)th input ECG sample of the plurality of input ECG samples from the first sum, wherein the first sum represents the sum of the Ath, (A−1)th, . . . (A−N+1)th input ECG samples of the plurality of input ECG samples, A and N being positive integers, A being greater than N; and divide the first sum by N to provide an intermediate sample of the plurality of intermediate samples.

17. The defibrillator of claim 16 wherein the second BCF is further configured to:

add an $\tilde{A}$th intermediate sample of the plurality of intermediate samples to a second sum and subtracting an ($\tilde{A}$−N)th intermediate sample of the plurality of intermediate samples from the second sum, wherein the second sum represents the sum of the $\tilde{A}$th, ($\tilde{A}$−1)th, . . . ($\tilde{A}$−N+1)th intermediate samples of the plurality of intermediate samples, $\tilde{A}$ being a positive integer greater than N; and divide the second sum by N to provide an estimated baseline wander sample of the plurality of estimated baseline wander samples.

18. The defibrillator of claim 17 wherein the delay circuit provides a delay of N+1 cycles.

19. The defibrillator of claim 18 wherein N is equal to 1024.

20. The defibrillator of claim 14 further comprising a plurality of electrodes, in addition to the pair of electrodes, coupled to the signal acquisition and digitizing circuit.

* * * * *